United States Patent
Glukhovsky et al.

(10) Patent No.: US 8,159,549 B2
(45) Date of Patent: Apr. 17, 2012

(54) SYSTEM AND METHOD FOR IN-VIVO IMAGING

(75) Inventors: Arkady Glukhovsky, Nesher (IL); Gavriel Meron, Petach Tikva (IL); Doron Adler, Nesher (IL); Ofra Zinati, Haifa (IL); Jerome Avron, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1107 days.

(21) Appl. No.: 11/025,111

(22) Filed: Dec. 30, 2004

(65) Prior Publication Data

US 2005/0110881 A1   May 26, 2005

Related U.S. Application Data

(63) Continuation of application No. 10/705,982, filed on Nov. 13, 2003, now Pat. No. 7,022,067, which is a continuation of application No. 09/571,326, filed on May 15, 2000, now Pat. No. 6,709,387.

(51) Int. Cl.
   *H04N 5/228* (2006.01)

(52) U.S. Cl. ...... 348/222.1; 348/22; 348/45; 348/220.1; 348/399.1; 348/412.1; 600/103; 600/105; 600/117; 600/118; 600/160

(58) Field of Classification Search ............... 348/22, 348/45, 65, 220.1, 222.1, 399.1, 412.1, 415.1; 600/103, 105, 117, 118, 160
See application file for complete search history.

(56) References Cited

U.S. PATENT DOCUMENTS

| | | | |
|---|---|---|---|
| 3,683,389 A | 8/1972 | Hollis | |
| 3,723,644 A | 3/1973 | Haskell et al. | |
| 3,888,237 A | 6/1975 | Mori | |
| 3,971,362 A | 7/1976 | Pope et al. | |
| 4,278,077 A | 7/1981 | Mizumoto | |
| 4,523,227 A | 6/1985 | Hurst et al. | |
| 4,629,424 A * | 12/1986 | Lauks et al. | ...... 433/6 |
| 4,689,621 A | 8/1987 | Kleinberg | |
| 4,741,327 A | 5/1988 | Yabe | |
| 4,844,076 A | 7/1989 | Lesho et al. | |
| 4,895,431 A | 1/1990 | Tsujiuchi et al. | |

(Continued)

FOREIGN PATENT DOCUMENTS

DE   34 40 177   5/1986

(Continued)

OTHER PUBLICATIONS

Partial European Search Report of Application No. 08 01 7205 mailed on Oct. 28, 2008.

(Continued)

*Primary Examiner* — Yogesh Aggarwal

(74) *Attorney, Agent, or Firm* — Pearl Cohen Zedek Latzer, LLP

(57) ABSTRACT

An in-vivo imaging device including a camera may include a frame storage device. Systems and methods which vary the frame capture rate of the camera and/or frame display rate of the display unit of in-vivo camera systems are discussed. The capture rate is varied based on physical measurements related to the motion of the camera. Alternatively, the frame capture rate is varied based on comparative image processing of a plurality of frames. The frame display rate of the system is varied based on comparative image processing of a multiplicity of frames. Both the frame capture and the frame display rates of such systems can be varied concurrently.

4 Claims, 9 Drawing Sheets

U.S. PATENT DOCUMENTS

| | | | |
|---|---|---|---|
| 4,953,539 A * | 9/1990 | Nakamura et al. | 600/109 |
| 5,098,426 A | 3/1992 | Sklar et al. | |
| 5,209,220 A | 5/1993 | Hiyama et al. | |
| 5,239,418 A | 8/1993 | Tyler et al. | |
| 5,262,871 A | 11/1993 | Wilder et al. | |
| 5,279,607 A | 1/1994 | Schentag et al. | |
| RE34,965 E | 6/1995 | Sugiyama | |
| 5,421,337 A | 6/1995 | Richards-Kortum et al. | |
| 5,452,004 A | 9/1995 | Roberts | |
| 5,604,531 A | 2/1997 | Iddan et al. | |
| 5,662,587 A | 9/1997 | Grundfest et al. | |
| 5,666,955 A | 9/1997 | Kondo et al. | |
| 5,748,232 A * | 5/1998 | Konuma | 348/219.1 |
| 5,784,099 A * | 7/1998 | Lippincott | 348/222.1 |
| 5,819,736 A | 10/1998 | Avny et al. | |
| 5,833,603 A | 11/1998 | Kovacs et al. | |
| 5,853,005 A | 12/1998 | Scanlon | |
| 5,993,378 A | 11/1999 | Lemelson | |
| 6,009,189 A | 12/1999 | Schaack | |
| 6,162,171 A | 12/2000 | Ng et al. | |
| 6,165,128 A | 12/2000 | Cespedes et al. | |
| 6,172,712 B1 | 1/2001 | Beard | |
| 6,228,030 B1 * | 5/2001 | Urbano et al. | 600/443 |
| 6,240,312 B1 | 5/2001 | Alfano et al. | |
| 6,402,686 B1 | 6/2002 | Ouchi | |
| 6,428,469 B1 | 8/2002 | Iddan et al. | |
| 6,475,145 B1 | 11/2002 | Baylor | |
| 6,493,466 B1 * | 12/2002 | Honda et al. | 382/236 |
| 6,603,981 B1 | 8/2003 | Carillo, Jr. et al. | |
| 6,632,175 B1 | 10/2003 | Marshall | |
| 6,719,684 B2 | 4/2004 | Kim et al. | |
| 6,738,265 B1 | 5/2004 | Svarfvar et al. | |
| 6,744,974 B2 | 6/2004 | Neuman | |
| 2001/0031005 A1 * | 10/2001 | Nister et al. | 375/240.16 |
| 2001/0035902 A1 | 11/2001 | Iddan et al. | |
| 2001/0051766 A1 | 12/2001 | Gazdzinski | |
| 2002/0080881 A1 | 6/2002 | Honda et al. | |
| 2002/0103417 A1 | 8/2002 | Gazdzinski | |
| 2002/0191113 A1 | 12/2002 | Siefken | |
| 2002/0198439 A1 | 12/2002 | Mizuno | |
| 2003/0013370 A1 | 1/2003 | Glukhovsky | |
| 2003/0069474 A1 | 4/2003 | Couvillon, Jr. | |
| 2003/0167000 A1 | 9/2003 | Mullick et al. | |

FOREIGN PATENT DOCUMENTS

| | | |
|---|---|---|
| EP | 0 667 115 | 8/1995 |
| EP | 0677272 A1 | 10/1995 |
| IL | 122602 | 4/2005 |
| JP | 49-114940 | 11/1974 |
| JP | 4109927 | 4/1992 |
| JP | 1992-144533 | 5/1992 |
| JP | 5015515 | 1/1993 |
| JP | 06-114037 | 4/1994 |
| JP | 10136252 | 5/1998 |
| JP | 2000-083182 | 3/2000 |
| JP | 2001-224553 | 8/2001 |
| JP | 3-289779 | 3/2004 |
| JP | 4-180736 | 7/2004 |
| WO | WO 92/21307 | 12/1992 |
| WO | WO 98/11816 | 3/1998 |
| WO | WO 99/22640 | 5/1999 |
| WO | WO 99/30610 | 6/1999 |
| WO | WO 00/22975 | 4/2000 |
| WO | WO 01/08548 | 2/2001 |
| WO | WO 01/50941 | 7/2001 |
| WO | WO 01/53792 | 7/2001 |
| WO | WO 01/65995 | 9/2001 |
| WO | WO 01/87377 | 11/2001 |
| WO | WO 02/26103 | 4/2002 |

OTHER PUBLICATIONS

Supplementary Partial European Search Report for EP 01 92 9965 dated May 10, 2006.

International Search Report for International Application No. PCT/IL01/00427 date of mailing Sep. 19, 2002.

"Machine Vision: Theory, Algorithms, Practicalities"—E.R. Davies, 2005.

"Non-Lambertian Shading and Photometric Stereo"—Tagare, et al., SPIE vol. 1260 Sensing and Reconstruction of Three-Dimensional Objects and Scenes (1990).

"Robust shape reconstruction from combined shading and stereo information"—Lee, et al., SPIE vol. 1771 Applications of Digital Image Processing XV (1992), pp. 171-182.

"Shedding light on cancer diagnosis"—Powell (Ed.), May 2000, Laser Focus World.

"Simulation of images by photometric stero modeling", Russell, et al., Optical Engineering, Sep. 1991, vol. 30, No. 9, pp. 1337-1345.

"Surface Representation from Photometric Stereo with Wavelets", Sinzinger, et al., SPIE vol. 3169, Jul. 30, 1997.

"The Radio Pill", Rowlands, et al., British Communications and Electronics, Aug. 1960, pp. 598-601.

"Two Image Photometric Stereo Method", Yang et al., SPIE vol. 1826, Intelligent Robots and Computer Vision XI (1992).

"Video Camera to "TAKE""—RF System lab, Dec. 25, 2001.

"Wellesley company sends body montiors into space"—Crum, 1998.

"Wireless transmission of a color television moving image from the stomach using a miniature CCD camera, light source and microwave transmitter". Swain CP, Gong F, Mills TN. Gastrointest Endosc 1997;45:AB40.

"BBC News Online—Pill camera to 'broadcast from the gut'", Feb. 21, 2000, www.news.bbc.co.uk.

"Estimating Motion in Image Sequences", Stiller et al., IEEE Signal Processing Magazine, Jul. 1999, pp. 70-91.

International Search Report of PCT/IL01/00427 dated Sep. 19, 2002.

Japanese Office Action, issued Oct. 27, 2010, for Japanese Application No. 2006-136080.

European Office Action for Application No. 02795412, mailed on Mar. 1, 2011.

Office Action for Japanese Application No. 2006-136080, mailed on Apr. 25, 2011.*

Shin-ichi et al.,"Robots for the future". Nipponia 13, Nov. 29, 2001.

"www.rfnorkia.com"—NORIKA3, Dec. 24, 2001.

Y. Bar-Cohen, Ed., "Electroactive Polymer Actuators as Artificial Muscles" SPIE Press, Bellingham, Washington; 2001.

Hannan et al., "The 'Elephant Trunk' Manipulator, Design and Implementation", pp. 1-6.

* cited by examiner

SYSTEM AND METHOD FOR IN-VIVO IMAGING

CROSS REFERENCE TO RELATED APPLICATIONS

This application is a continuation application of U.S. Ser. No. 10/705,982, filed on Nov. 13, 2003 now U.S. Pat. No. 7,022,067 and entitled "SYSTEM AND METHOD FOR CONTROLLING IN VIVO CAMERA CAPTURE AND DISPLAY RATE", which in turn is a continuation application of U.S. Ser. No. 09/571,326, filed on May 15, 2000 now U.S. Pat. No. 6,709,387 and entitled "SYSTEM AND METHOD FOR CONTROLLING IN VIVO CAMERA CAPTURE AND DISPLAY RATE", each of which being incorporated in its entirety by reference herein.

FIELD OF THE INVENTION

The present invention relates generally to an in-vivo camera system and, in particular, to a system and method for controlling the frame capture rate and frame display rate of images produced by such a camera system.

BACKGROUND OF THE INVENTION

Several in-vivo measurement systems are known in the art. They include swallowable electronic capsules which collect data and which transmit the data to a receiver system. These intestinal capsules, which are moved through the digestive system by the action of peristalsis, are used to measure pH ("Heidelberg" capsules), temperature ("CoreTemp" capsules) and pressure throughout the gastrointestinal (GI) tract. They have also been used to measure gastric residence time, which is the time it takes for food to pass through the stomach and intestines. These intestinal capsules typically include a measuring system and a transmission system, where a transmitter transmits the measured data at radio frequencies to a receiver system.

Endoscopes are other types of devices that obtain images from the gastrointestinal tract. There are currently two types of endoscopes. Fiber-optic endoscopes are pushed through the GI tract and use a fiber optic waveguide to transmit a light signal from the area of interest to electronics located outside the patient's body. Video endoscopes place an electronic camera at the area of interest and transfer the video data through a flexible cable to electronics located externally.

U.S. Pat. No. 5,604,531, assigned to the common assignee of the present application and incorporated herein by reference, teaches an in-vivo measurement system, in particular an in-vivo camera system, which is carried by a swallowable capsule. In addition to the camera system there is an optical system for imaging an area of the GI tract onto the imager and a transmitter for transmitting the video output of the camera system. The overall system, including a capsule that can pass through the entire digestive tract, operates as an autonomous video endoscope. It images even the difficult to reach areas of the small intestine.

Reference is now made to FIG. 1 which shows a block diagram of the in-vivo video camera system described in U.S. Pat. No. 5,604,531. The system captures and transmits images of the GI tract while passing through the gastrointestinal lumen. The system contains a storage unit 19, a data processor 14, a camera 10, an image transmitter 8, an image receiver 12 (often an antenna array), which usually includes an antenna array, and an image monitor 18. Storage unit 19, data processor 14, image monitor 18, and image receiver 12 are located outside the patient's body. Camera 10, as it transits the GI tract, is in communication with image transmitter 8 located in capsule 6 and image receiver 12 located outside the body. Data processor 14 transfers frame data to and from storage unit 19 while the former analyzes the data. Processor 14 also transmits the analyzed data to image monitor 18 where a physician views it. The data can be viewed in real time or at some later date.

The number of pictures that need to be taken and which must be analyzed by the attending physician is great. Assuming a minimum of two images per second and a four to five hour dwell time in the GI tract, 30,000 images would be required during the transit of the GI tract by the capsule. If 20 frames per second (fps) are displayed as is standard, the physician would need about 30 minutes to examine the images of the entire GI lumen.

PCT Application PCT/IL98/00608, published as WO 99/30610 and Israeli Application 122602 assigned to the common assignee of the present application and incorporated herein by reference, recite a method for reducing the number of frames captured by an in-vivo camera, thereby extending its life. The method discussed in the aforesaid applications requires disconnecting the camera 10 from the power source when motion (velocity) is below a certain threshold value.

SUMMARY OF THE PRESENT INVENTION

It is an object of the present invention to provide a system and method for minimizing the time for reviewing images taken by an in-vivo camera system or by endoscopes. This is accomplished by either varying the rate of data display and/or varying the rate of data acquisition.

In one embodiment of the present invention, an in-vivo camera system includes an imager which can have its frame capture rate varied. It also includes at least one sensor for measuring a physical property relatable to the motion of the camera system, a data processor for determining a frame capture rate after receiving data from the sensor, and a controller for supplying the determined frame capture rate to the imager. The sensor can be, among other things, an accelerometer, an accelerometer connected to an integrator, a pressure sensor, an induction coil, or an ultrasonic transducer.

In another embodiment, an in-vivo camera system includes an imager which can have its frame capture rate varied, a storage device for storing frames captured by the imager, an image processor for calculating the required frame capture rate from at least two frames, and a controller for supplying the calculated frame capture rate to the imager.

In yet another embodiment of the present invention, a display system for displaying the output of an in-vivo camera system is described. The system includes a frame storage unit for storing frames of the camera system, and an image processor for correlating frames to determine the extent of their similarity. The processor generates a frame display rate which is slower when the frames are generally different and faster when the frames are generally similar. The embodiment also includes a display unit for displaying the frames received from the frame storage unit at the frame display rate. The display system described can also include a controller connected to a frame storage unit and the imager processor. The controller then varies the display rate of the aforementioned display unit. In the above embodiment the at least two frames can be consecutive or non-consecutive frames.

In still another embodiment a video camera system also includes a display system having a frame storage unit for storing at least two frames and an image processor for determining the similarity of at least two frames. The processor generates a frame display rate based on the similarity of the frame. The frame display rate is slower when the frames are generally different and faster when the frames are generally similar. The embodiment also includes a display unit for displaying the frames received from the frame storage at the required frame display rate.

In yet another embodiment an in-vivo camera system also includes a display system having a frame storage unit for storing at least two frames. The display system further includes an image processor for correlating at least two frames thereby determining the extent of their similarity and for generating a frame display rate based on that similarity. Finally, the display system includes a display unit for displaying the frames received from the frame storage at the frame display rate.

In one embodiment of the present invention, a method is taught for varying the frame capture rate of a series of frames generated by an in-vivo camera system. The method includes the steps of storing the frames in a storage device, correlating changes in the details of at least two frames, changing the frame capture rate to a predetermined frame capture rate according to the degree of change between the at least two frames and transmitting the capture rate to the imager.

In another embodiment, a method is taught for varying the frame capture rate of a series of frames generated by an in-vivo camera system. The method includes the steps of measuring a physical quantity experienced by the camera system, converting the physical quantity to a velocity of the camera, correlating the velocity with a predetermined frame capture rate, and transmitting the predetermined capture rate to the imager. The step of measuring includes the step of measuring acceleration, pressure, induced current or motion, the latter with an ultrasonic transducer.

In yet another embodiment of the present invention, a method is taught for varying the frame display rate of a series of frames generated by an in-vivo camera system, the method including the steps of storing the frames in a storage device, correlating changes in the details of at least two frames, and transmitting the required frame display rate to a storage device and a display unit.

Yet a further embodiment of the present invention teaches a method for varying the frame display rate of a series of frames generated by an in-vivo camera system which includes the step of repeating the display of a frame a predetermined number of times.

A similar further embodiment teaches a method for varying the frame display rate of a series of frames generated by an in-vivo camera system which includes the step of eliminating the display of at least one frame.

The system may include an imager for producing frames and a storage device for storing frames.

BRIEF DESCRIPTION OF THE DRAWINGS

The present invention will be understood and appreciated more fully from the following detailed description taken in conjunction with the drawings in which.

Similar elements in different figures are given identical numbers throughout.

DETAILED DESCRIPTION OF PREFERRED EMBODIMENTS

The large volume of data collected by an in-vivo camera system, such as the one described above, is a result of the long period of time, usually several hours, that it takes the camera to traverse the gastro-intestinal tract. The camera transits the GI tract in fits and starts. Because of the intermittent motion of the capsule and its long residence time at some positions, the number of sequential images that are similar is very large. It would be preferable if such duplicative frames were eliminated entirely or at least reduced in number. Alternatively, the display time of individual frames can be shortened, thereby reducing the time required to view the image data stream. The present invention describes a number of ways to shorten viewing time: reducing the frame capture rate (FIGS. 2-4) and/or reducing the frame display rate (FIG. 5).

It should be understood that in all discussions both above and below, when the terms camera and imager are used they are equivalent. It should also be understood that the camera or imager being discussed in this application is one capable of having its frame capture rate and/or frame display rate varied.

Figure 2:
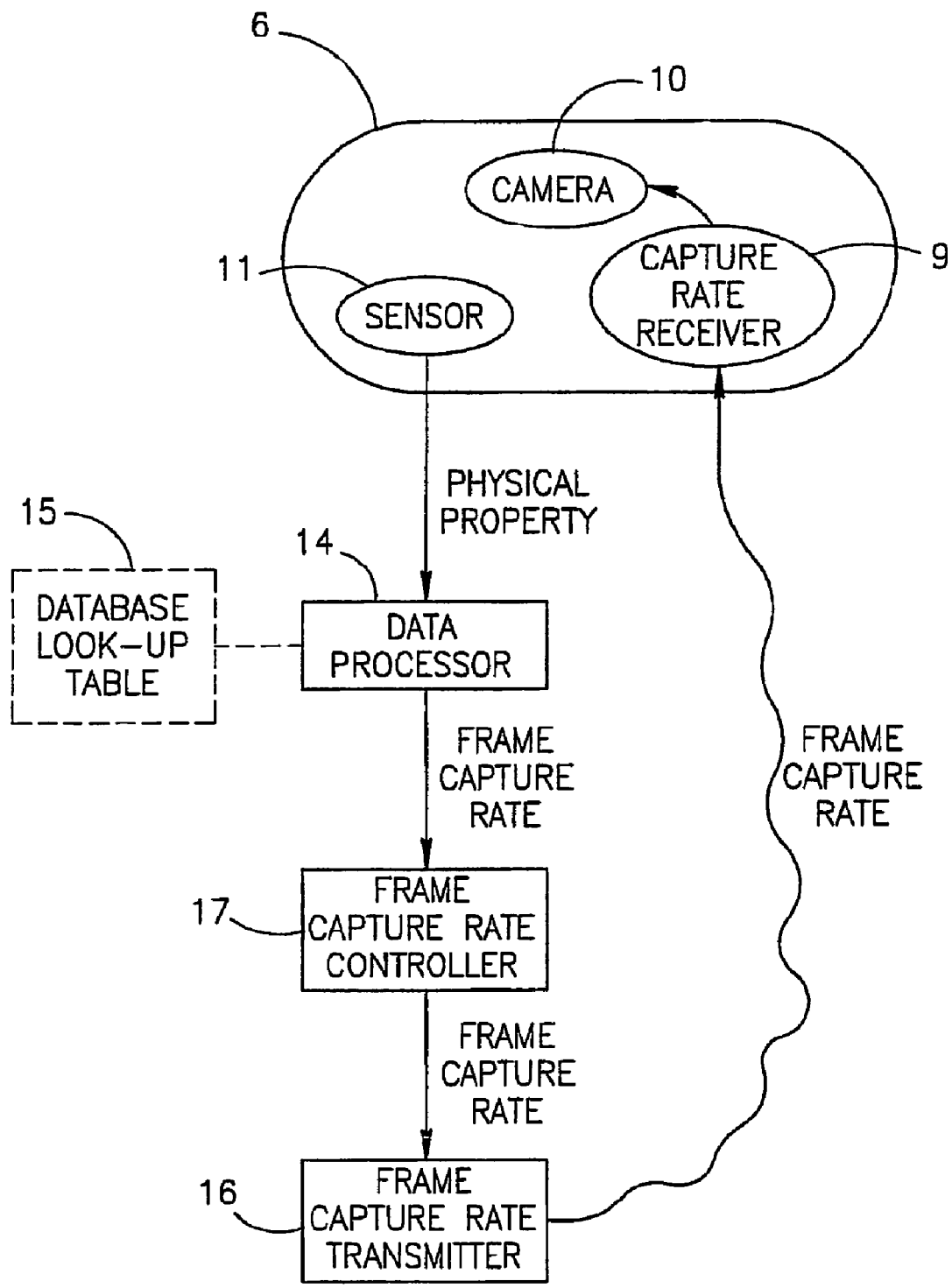
FIG. 2 is a block diagram illustration of a system for varying the frame capture rate of the camera system of FIG. 1 using a sensor to determine changes in video capsule velocity.

One method to control the frame capture rate is to monitor the velocity of the capsule in the GI tract. Reference is now made to FIG. 2, which illustrates, in block diagram format, a system for controlling the frame capture rate of the camera 10. The system comprises a sensor 11, a data processor 14, a frame capture rate controller 17, a frame capture rate transmitter 16, a capture rate receiver 9, camera 10 and optionally, a database or look-up table 15. Camera 10 and capture rate receiver 9 are both located within the capsule.

Sensor 11, which measures motion directly or indirectly, is attached to, or placed within, the capsule 6 and relays the value of a measured motion-related physical property to data processor 14. Data processor 14, together with database (or a look-up table) 15 to which processor 14 is linked, determines the required frame capture rate based on current and past values of the measured property. When the camera is moving slowly, fewer frames need to be captured; when it moves quickly, the number of frames captured or displayed needs to be increased. Data processor 14 then provides the calculated capture rate to frame capture rate controller 17, which, in turn, transmits the rate to camera 10. For clarity, FIG. 2 (as well as all later Figures) does not show the image transmitter 8 and image receiver 12 described above which is the actual link between sensor 11 and data processor 14.

In the above embodiment, a database or look-up table is used. In other embodiments, database or look-up table 15 is not needed and processor 14 calculates the required frame capture rate directly using a suitable function.

FIG. 2 illustrates how the capture rate is transmitted to camera 10. Frame capture controller 17 transfers the desired frame capture rate to frame capture rate transmitter 16. Both controller 17 and transmitter 16 are outside the patient's body. Transmitter 16 transmits information about the required capture rate to capture rate receiver 9 located within capsule 6. Capture rate receiver 9 then adjusts the frame capture rate of camera 10.

Figure 3A:
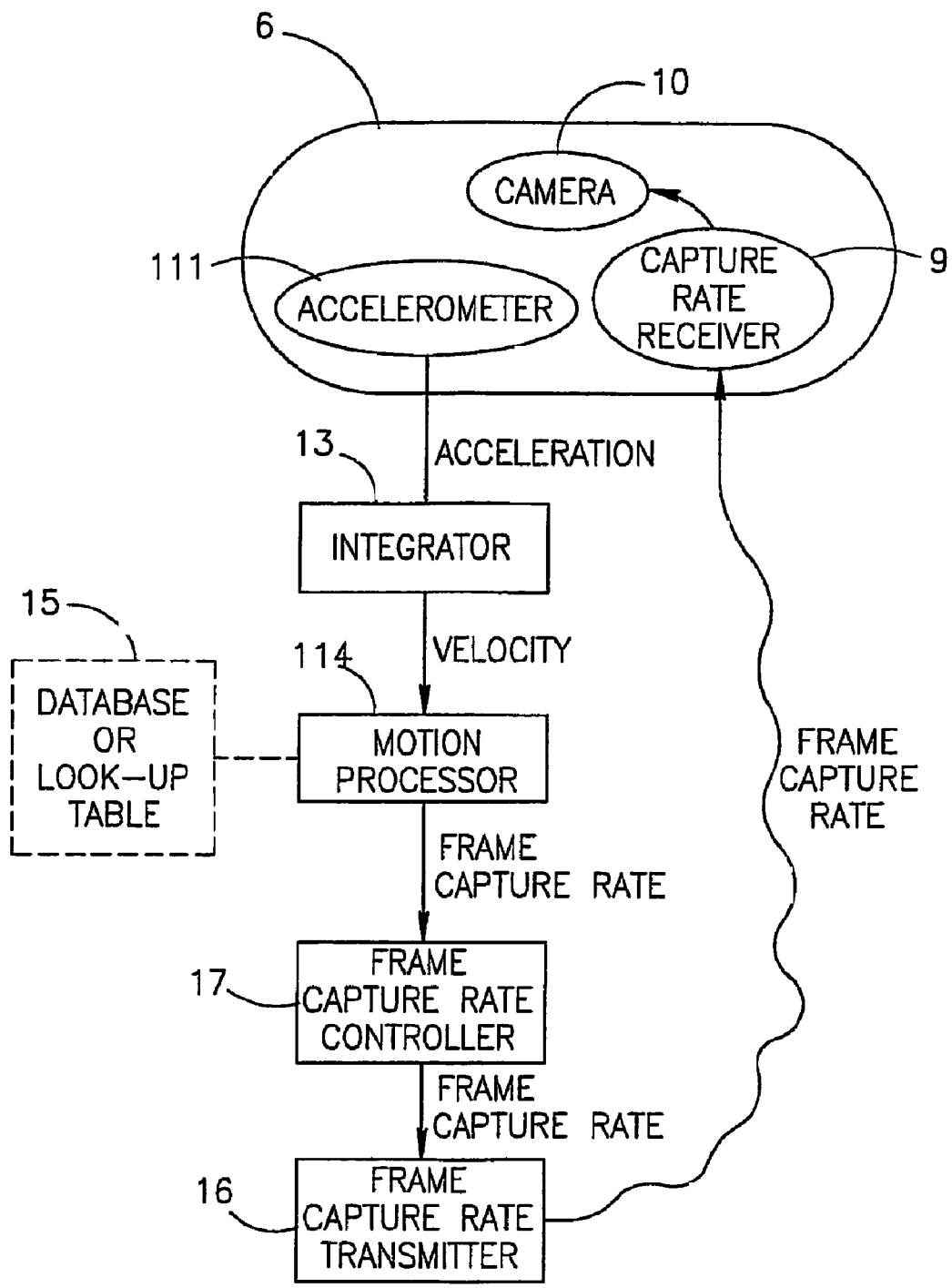
FIG. 3A is a block diagram illustration of a further embodiment of FIG. 2 using an accelerometer as a sensor.

A special case of the system in FIG. 2 is illustrated in FIG. 3A where the sensor is an accelerometer 111 whose output is processed by an integrator 13. The processor is a motion processor 114. The remaining elements are as shown in FIG. 2. Accelerometer 111 is in communication with integrator 13. Accelerometer 111, which is typically placed in the interior of capsule 6, determines the instantaneous acceleration of capsule 6 as it moves through the GI tract. Integrator 13 converts the acceleration data to velocity. Integrator 13 can be a stand-alone element connected to motion processor 114 (as in FIG. 3A) or it can be an integral part of motion processor 114. In either case, integrator 13 transfers information regarding the velocity of the capsule to motion processor 114. Motion processor 114, together with database (or look-up table) 15, determines the required frame capture rate. Processor 114 relays the calculated capture rate to frame capture rate controller 17. As described above (FIG. 2), frame capture controller 17 relays the required frame capture rate via frame capture rate transmitter 16 to capture rate receiver 9 within capsule 6.

In lieu of database (or look-up table) 15 in FIG. 3A, motion processor 114 can utilize a function that relates velocity to frame capture rate. The function can then be used to calculate the required rate. The function, capture rate vs. capsule velocity, will usually be monotonically increasing.

The small accelerometer 111 used in FIG. 3A can be purchased from numerous suppliers. A suitable integrator 13 can also be obtained from many different vendors. Alternatively, an integrator can be built using an operational amplifier or implemented numerically using an A/D converter and a microprocessor.

In another embodiment, the integrator can be omitted from FIG. 3A. In that case, data from the accelerometer 111 can be processed directly to determine the required frame capture rate.

Figure 1:
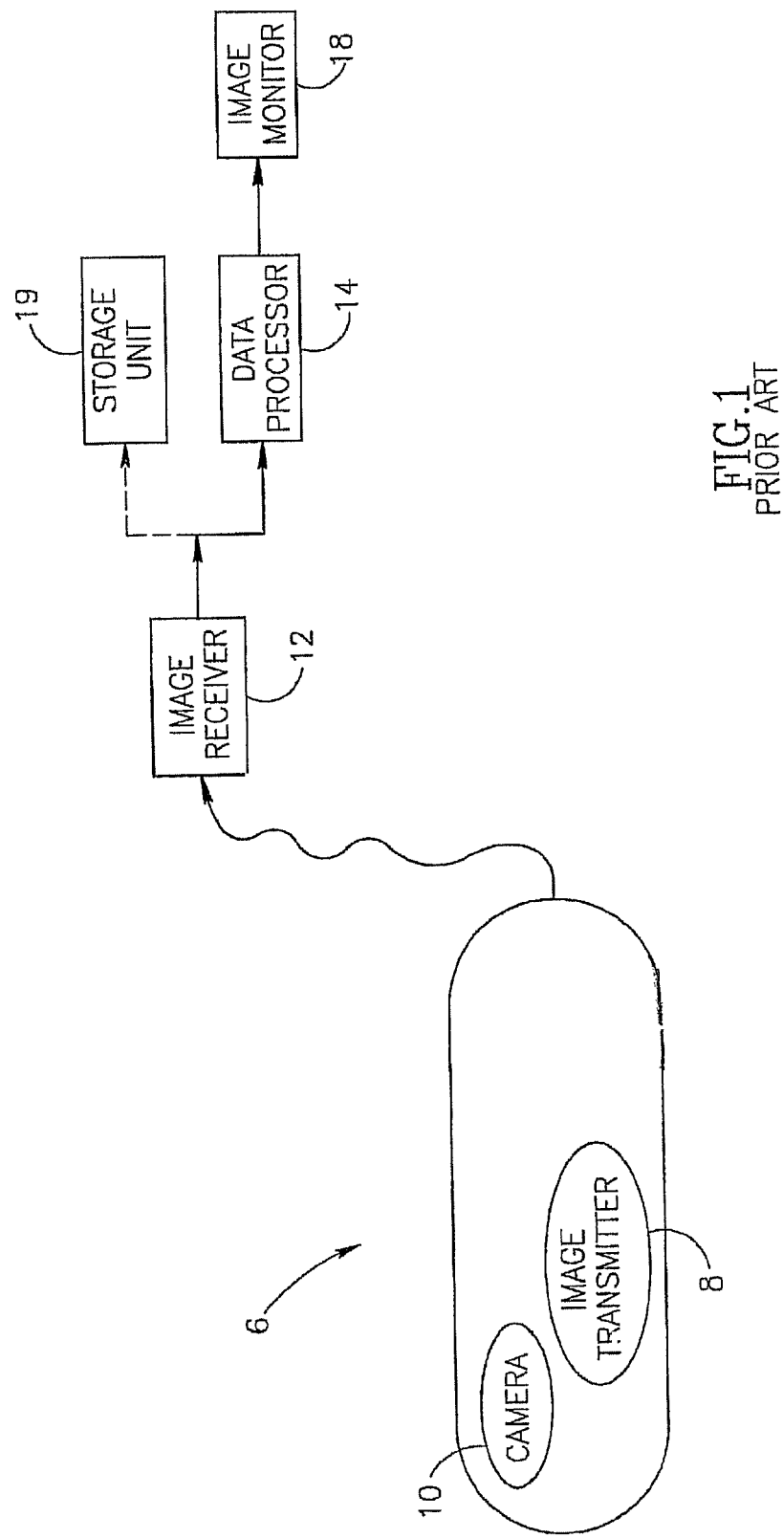
FIG. 1 is a block diagram illustration of a prior art in-vivo video camera system.

The system in FIG. 1 has been shown and described with processing and storage units outside the body, but they do not have to be. Through miniaturization of the components, most, if not all, electronic elements in FIGS. 2 and 3A above and FIGS. 4, 5 and 8 below, can be attached to or placed within capsule 6 and in direct communication with camera 10.

Figure 3B:
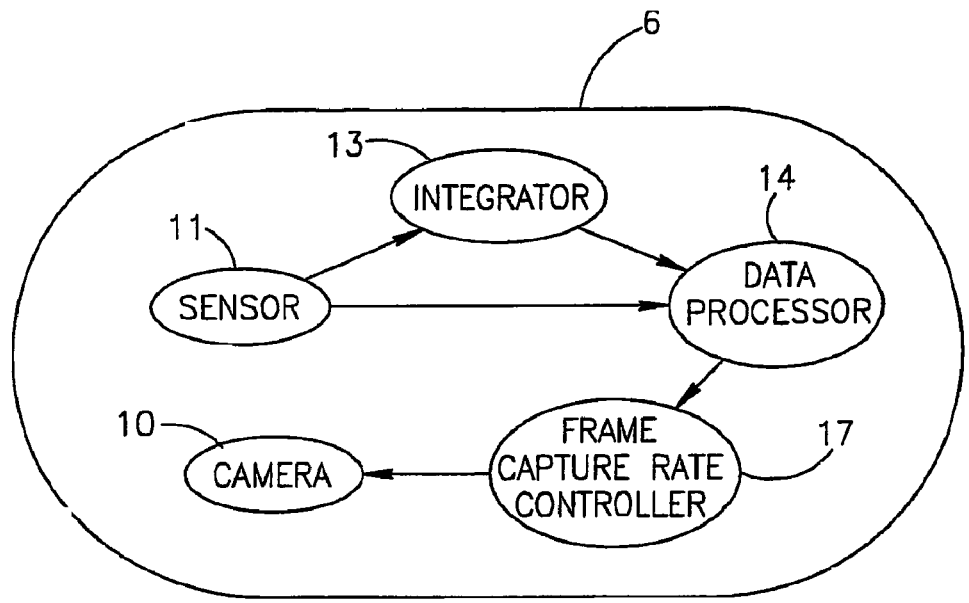
FIG. 3B is a block diagram illustration of a still further embodiment of FIG. 2 using an accelerometer as a sensor with the control loop and sensor all inside the capsule.

In fact, for the embodiments illustrated in FIGS. 2 and 3A, a similar but alternate placement of components is possible. Referring to FIG. 3B, the previous embodiments would have sensor 11 (or accelerometer 111), integrator 13, data processor 14, and frame rate controller 17 positioned inside capsule 6 and in direct communication with camera 10. Frame rate transmitter 16 and capture rate receiver 9 would then be superfluous.

Other sensors can be used which can determine velocity. A pressure sensor attached to the capsule is one such sensor. When the rate of peristalsis increases, velocity of the capsule through the small intestine increases. A pressure sensor can detect peristaltic induced pressure (and/or changes in pressure) exerted by the walls of the small intestine. The relation between pressure (and/or changes in pressure) and velocity can be determined empirically, and then utilized to determine the frame capture rate.

If the patient is placed in a magnetic field, capsule 6 can contain an induction coil which functions as a velocity sensor. The magnetic field induces a current in the coil whose magnitude is a function of the velocity of the coil through the field. Data on the induced current is transmitted to motion processor 114 and processed as in FIG. 3A.

While the sensors 11 discussed with FIGS. 2 and 3 above are in-vivo sensors and are attached directly to capsule 6, external sensors can also be used. A Doppler ultrasound unit continuously tracking the capsule can serve as an external sensor. Such a unit would be in communication with motion processor 114 which would process velocity data and convert it to a frame capture rate as discussed hereinabove. The conversion of ultrasonic Doppler data to velocity data is well-known in the art. Once the velocities have been calculated, a function, database or look-up table can be used to define the desired capture rate.

In yet another embodiment, several physical properties are measured concurrently and used to determine an optimum frame capture rate. This embodiment requires multiple sensors 11, each attached to the capsule 6, or possibly, as with an ultrasound sensor, outside the body. Each sensor would measure a different property. A data processor 14 or 114 as in FIGS. 2 and 3, or even a set of processors 14, one for each property being measured, interprets the data and determines a suitable frame capture rate. The analyses performed by the several processors are relayed to a central command processor (not shown) where their results are combined to obtain an optimum overall frame capture rate. The overall optimal rate is then relayed from the central command processor to frame capture rate controller 17, which transmits it to camera 10 in a manner identical to that described in FIG. 2.

In all of the above embodiments where the velocity of the capsule is determined, the conversion of velocity data to frame capture rate does not necessarily require the use of digital data. Analog data provided by the sensor may be used directly to determine the required frame capture rate if proper ancillary analog circuitry is employed.

Figure 4:
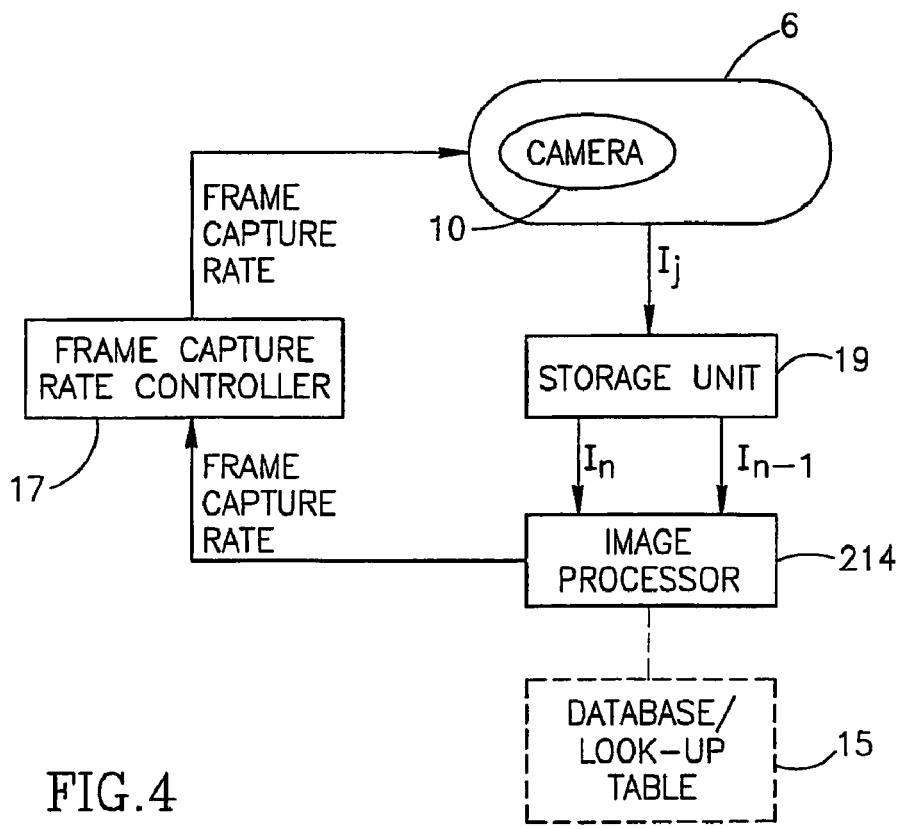
FIG. 4 is a block diagram illustration of an alternative embodiment of the system of FIG. 1 in which image data from two consecutive frames is compared.
Figure 5:
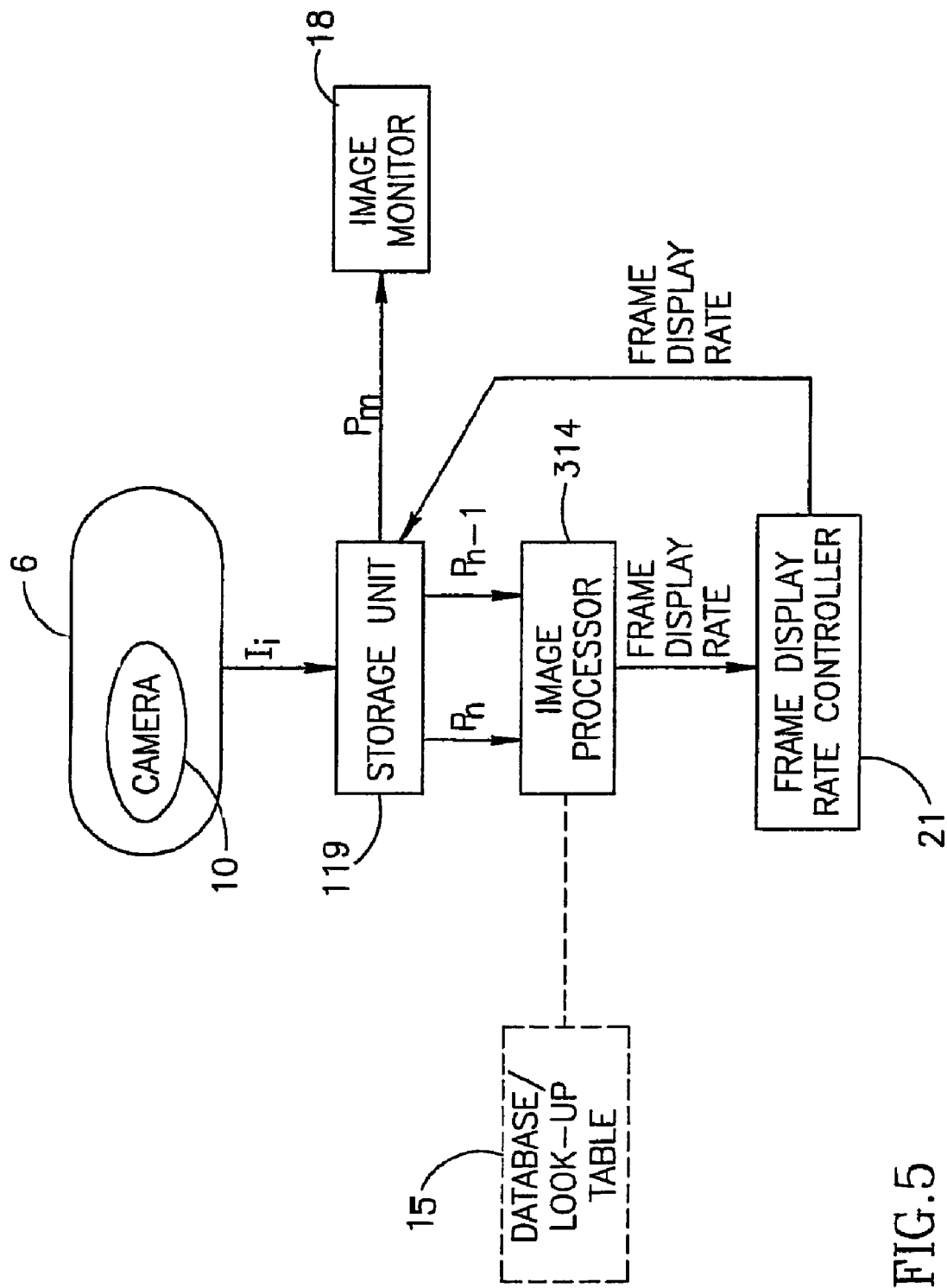
FIG. 5 is a block diagram illustration for varying the frame display rate of the in-vivo video camera system of FIG. 1 by comparing image data from two consecutive frames.

Reference is now made to FIG. 4 which illustrates another method for varying the frame capture rate. FIG. 4 shows camera 10, storage unit 19, an image processor 214, frame capture controller 17 and optionally, database or look-up table 15. Camera 10 captures a frame that is transmitted as described in FIG. 1 to external storage unit 19. Images are stored sequentially in unit 19. The stored data is comprised of one or more pixel properties. Color and intensity are among the properties that can be stored.

Image processor 214 receives images for comparison from storage unit 19. Processor 214 compares each image $I_n$ in the data stream to its predecessor $I_{n-1}$. If the stream of images is too lengthy or rapid, non-adjacent images can be compared, e.g. image $I_n$ with the image $I_{n-k}$, where k>1. For this latter embodiment, the capture rate can be calculated for each $k^{th}$ image, where k>0. As described below with respect to FIG. 6, the comparison can be made on a pixel-by-pixel basis or, alternatively, on a pixel cluster basis. Based on the comparison of the two images, processor 214 calculates the required frame capture rate.

Frame capture rate controller 17 receives information about the required frame capture rate from image processor 214. As shown in FIG. 2 and described above, controller 17 transfers the required frame capture rate to camera 10. For clarity, the requisite elements for this transfer have not been included in FIG. 4 but can be seen in FIG. 2.

All of the methods discussed above relate to the frame capture rate. An alternative approach for reducing overall presentation time of the datastream of the system is to use a variable frame display rate. In such situations, the frame capture rate can, but need not, be held constant. When the analysis of the pixels in consecutive frames indicates that the capsule is at rest or moving slowly, the images are displayed at a fast display rate. If the analysis indicates that the capsule is moving rapidly through the GI tract, the images are displayed more slowly.

Reference is now made to FIG. 5, where a block diagram illustrates such a system. The diagram shows camera 10, storage unit 119, an image processor 314, frame display rate controller 21, image monitor 18 and, optionally, database or look-up table 15. Camera 10 transmits frames to storage unit 119. After the acquisition of a given number of frames and their storage in the buffer of storage unit 119, two consecutive frames $P_n$ and $P_{n-1}$, are sent to image processor 314. The frames, either on a pixel-by-pixel or pixel cluster basis, are compared using a suitable function or set of functions. The function will usually be monotonically increasing. Image processor 314, based on its analysis of the compared frames, relays the required frame display rate to frame display controller 21. Frame display controller 21 provides the required frame display rate to storage unit 119. The latter releases an image $P_m$ or images $P_m$ through $P_{m+p}$ to image monitor 18. $P_m$ may, but need not be, frames $P_n$ or $P_{n-1}$. As discussed above, it should be remembered that the frame comparison need not be performed between adjacent images $P_n$ and $P_{n-1}$ but between $P_n$ and $P_{n-k}$, where k>1.

The functions used by image processors 214 and 314 in FIGS. 4 and 5 to make their determinations can be based on:

Calculating the simple difference in a given property between corresponding pixels of two, not necessarily consecutive, frames;

Calculating the cross-correlation function between two, not necessarily consecutive, frames; and Calculating the changes of local statistical distributions β and between corresponding local statistical distributions β in two, not necessarily consecutive, frames.

Local statistical distributions can include the mean, the variance or the standard deviation of given pixel clusters. The pixel cluster, for example, can be the pixels in the upper left quadrant (64×64 pixels) of a 256×256 image. The above approaches are illustrative only; other approaches may also be used.

When the image display rate is calculated for non consecutive images, $P_j$ and $P_{j+k}$, where k>1, the images $P_{j+1}$ and $P_{j+k-1}$, between the non-consecutive images are speeded up or slowed done as determined by the display rate calculation for frames $P_j$ and $P_{j+x}$.

Figure 6:
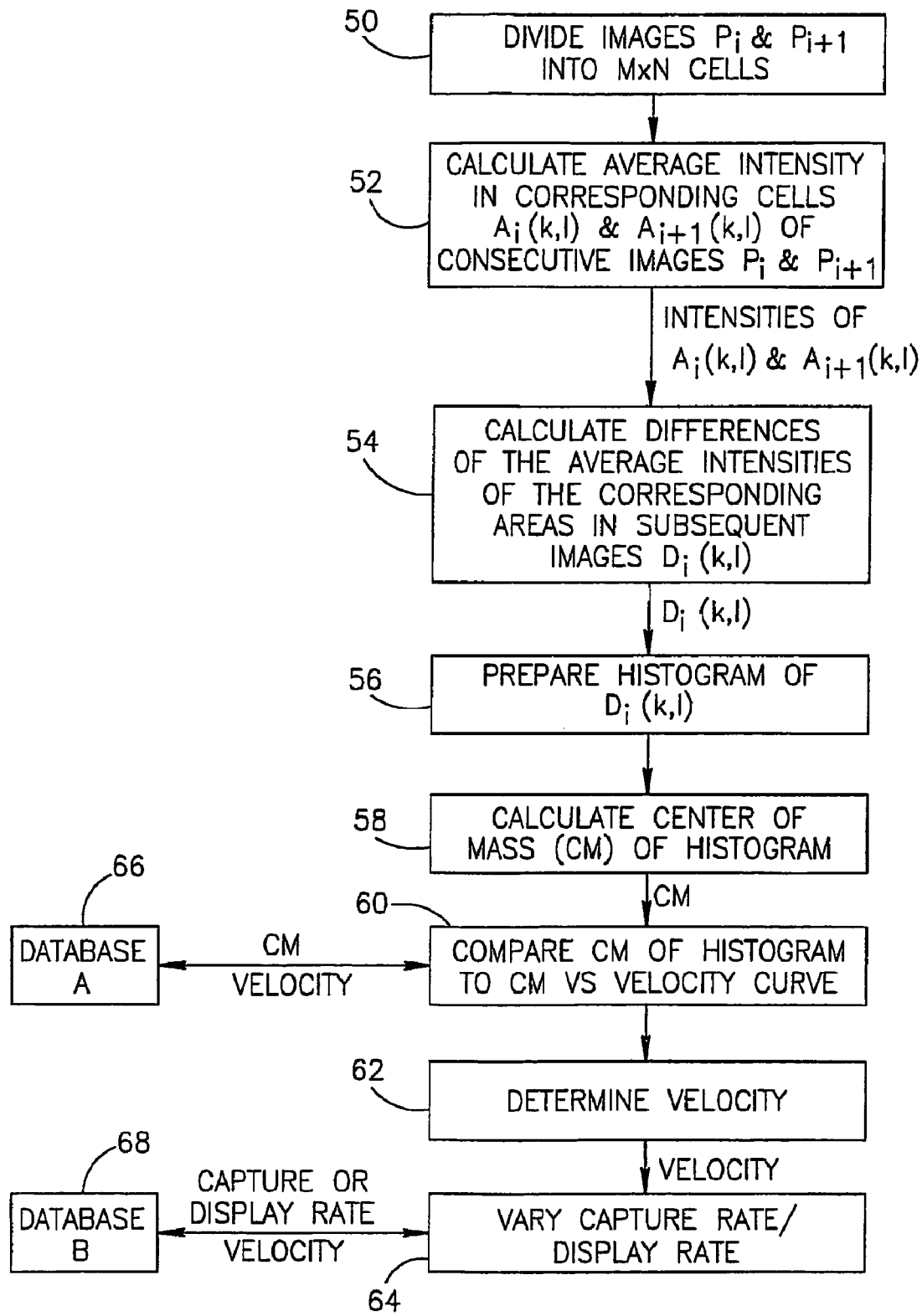
FIG. 6 is a block diagram illustration of a method for determining if the capsule has moved and a change in frame display rate is required.

Reference is now made to FIG. 6 where a block diagram of a function which can be used to determine the required display rate is illustrated. FIG. 6 shows the operations needed for comparing image $P_i$ and $P_{i+x}$, where x is usually, but not necessarily, 1. Initially, each image $P_i$ is divided (step 50) into a multiplicity of cells $A_i$(m,n), where 1<m<M and 1<n<N.

The average intensity, $I_{Ai(m,n)}$ of each cell $A_i$(m,n) of image $P_i$ is then calculated (step 52) from data provided by image receiver 12 of FIG. 1. The absolute value of the difference $D_i$(k,l) of the average intensities I of $A_i$(k,l) and $A_{i+x}$(k,l) of corresponding cells A(k,l) in frames $P_i$ and $P_{i+x}$ is determined (step 54). $D_i$(k,l) is defined as:

$$D_i(k,l) = |I_{A_i(k,l)} - I_{A_{i+x}(k,l)}|$$

It is readily apparent that where $D_i$(k,l) is small, the capsule is moving slowly.

Figure 7:
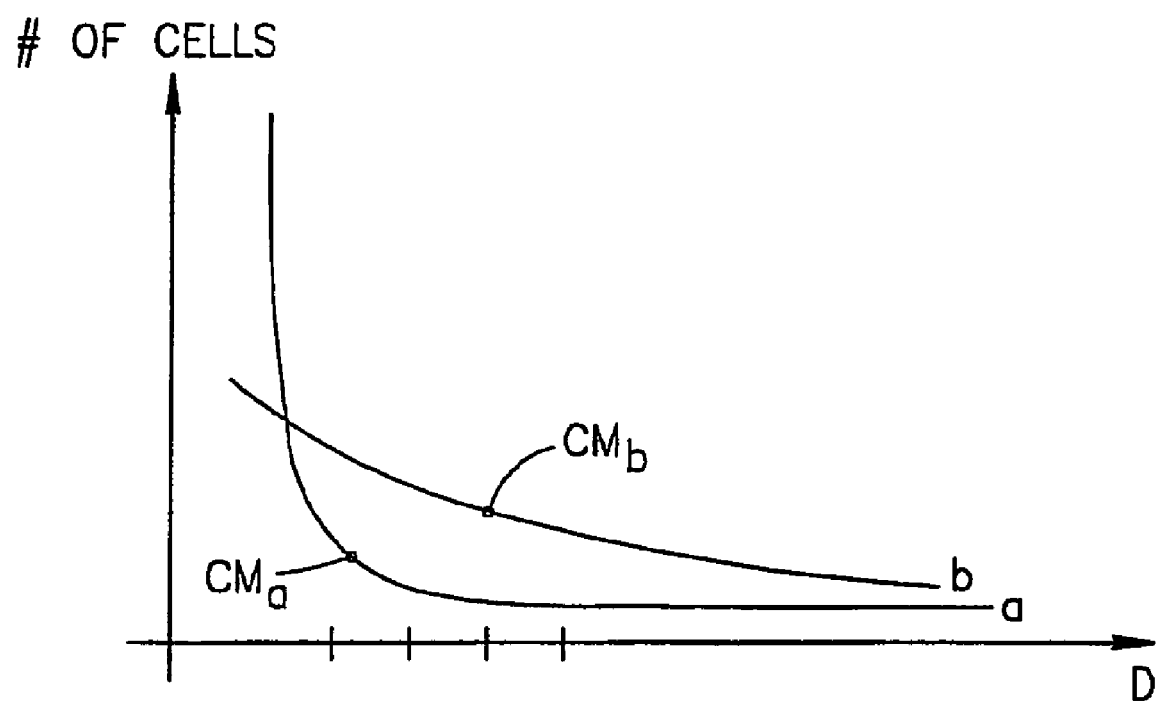
FIG. 7 are histogram illustrations of a difference function useful in understanding the method of FIG. 6.

The $D_i$(k,l) values are then organized into a histogram (step 56). The y-axis of the histogram is $D_i$(k,l) and the x-axis is the number of corresponding pairs of cells, $A_i$(k,l) and $A_{i+x}$(k,l), which have a difference of magnitude $D_i$(k,l). Referring to FIG. 7, curve (a) represents a histogram of essentially similar cells in consecutive (or non-consecutive) frames, while curve (b) shows a histogram of cells in significantly different frames. It should readily be apparent that if two images are similar, the histogram of the differences in the cells of these images are concentrated at low values of $D_i$(k,l). If the images are different, the histogram contains higher values of $D_i$(k,l). It should also be readily apparent that the center of mass $CM_a$ of curve (a) is further to the right than the $CM_b$ of curve (b) and represents a slower moving capsule.

Returning to FIG. 6, the center of mass CM of the histogram is determined in step 58. The CM of the histogram can be correlated (step 60) with the velocity of the capsule by using an empirically determined correlation supplied (step 66) by a database or look-up table. On the basis of the CM of the histogram, a difference between images is determined and a velocity calculated (step 62). The capture or display rate as a function of the difference or similarity in the compared images can be provided (step 68) from another empirically developed database, look-up table or mathematical function. The capture or display rate is then varied (step 64) accordingly.

Figure 8A:
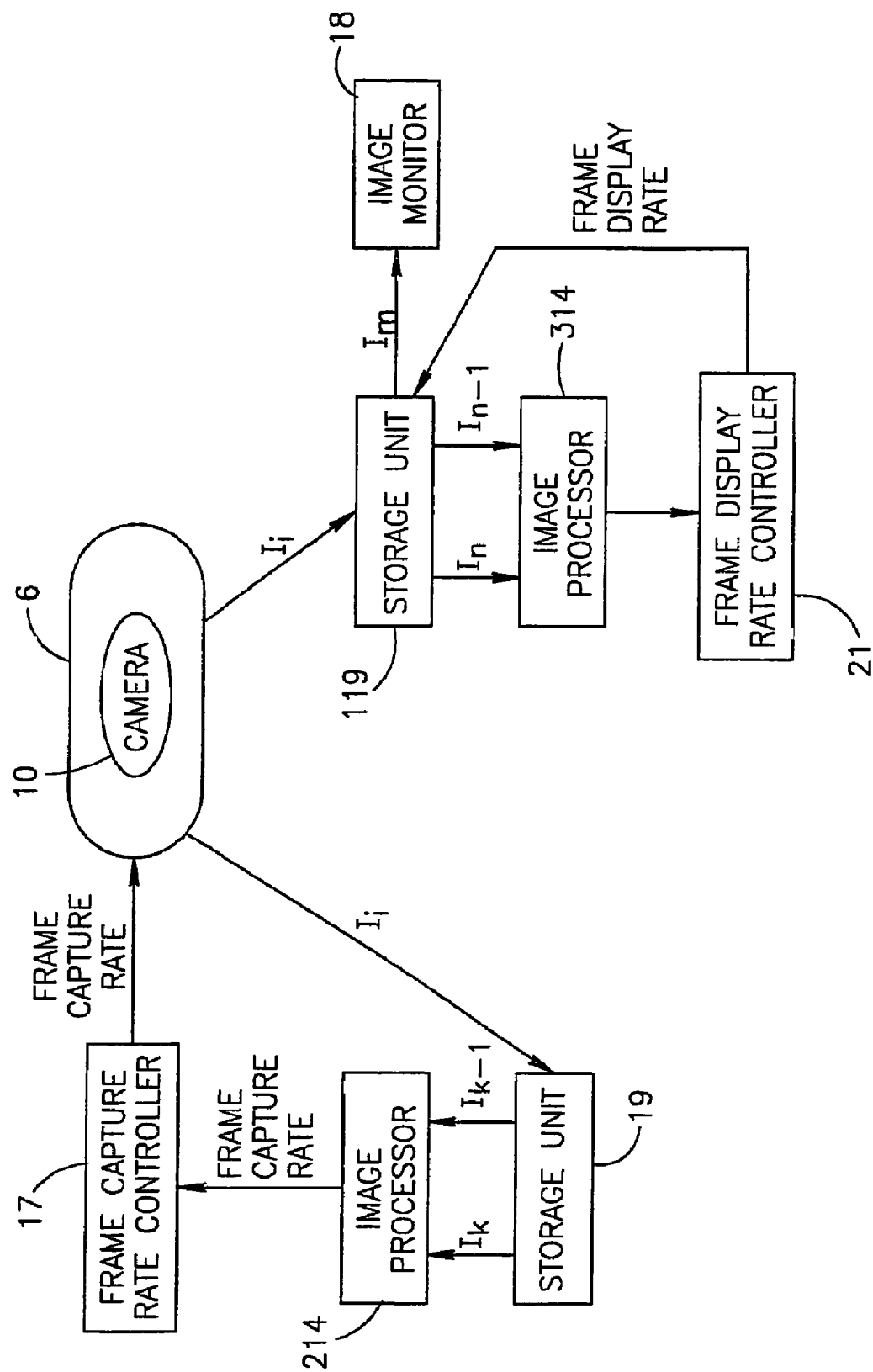
FIG. 8A is a block diagram illustration of a method for varying both the frame display rate and the frame capture rate as described in FIGS. 4 and 5.
Figure 8B:
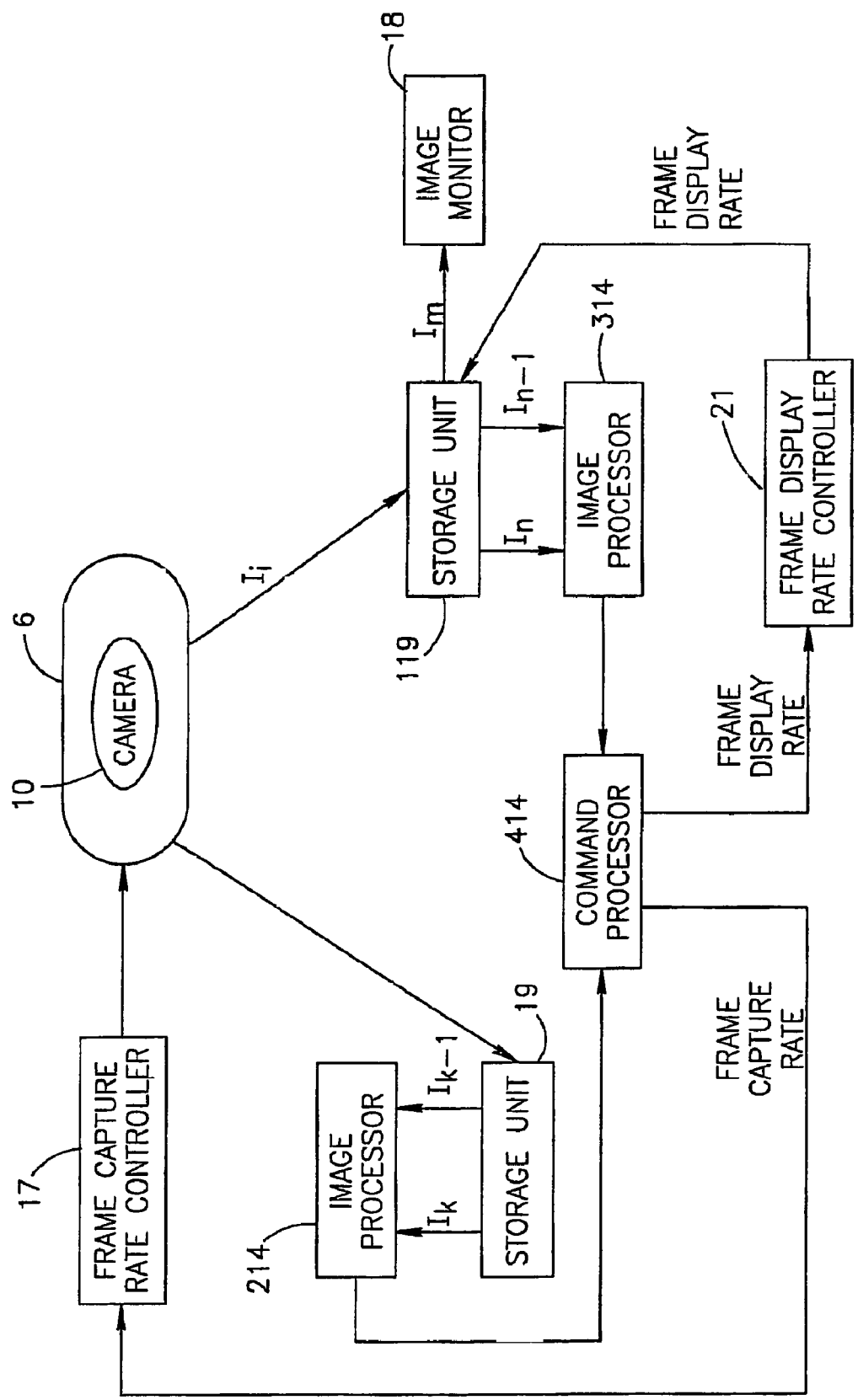
FIG. 8B is a block diagram illustration of a system as in FIG. 8A but also including a command processor.

Reference is now made to FIGS. 8A and 8B, which illustrate yet another embodiment of the invention. FIG. 8A shows a combined system where both the frame capture rate and the frame display rate are varied concurrently to minimize total data stream display time. FIG. 8A is a fusion of the systems shown in FIGS. 4 and 5. There could equally well have been a combined system of the embodiments described in FIG. 2 or 3 and 5.

In FIG. 8A, two storage units 19 and 119 and two image processors 214 and 314 are shown. The system also includes frame capture rate controller 17, frame display rate controller 21, image monitor 18 and camera 10. One storage unit 19 stores data for the frame capture rate analysis while the other unit 119 stores data for the frame display rate calculation. Each image processor 214 and 314 processes a different rate calculation. Image processors 214 and 314 could use the same or different algorithms to calculate the required capture and display rates.

FIG. 8B is similar to FIG. 8A but contains a command processor 414 which coordinates and optimizes the capture and display rate calculations, while minimizing total presentation time. The command processor 414 receives results calculated by processors 214 and 314 and transfers the optimized overall rates to capture and display controllers 17 and 21 respectively.

Currently, data is collected by the video camera at a rate of 2 frames per second (fps) and screened at a normal video rate of 30 fps. This screening rate is too fast for the eye to discern changes and the display rate must be slowed. An alternative to slowing down the display rate is to repeat the same frame several times, displaying the repeated frames at the standard rate. Repeating a frame is a way of changing the display rate in cases where it is impossible to change the display rate of individual frames directly. Methods such as those discussed above, which measure the difference between corresponding pixels in two frames, can be used to determine if repetitive screening of the same frame is required. Repetition of frames, however, increases the total length of the data stream. Therefore, the processor must determine when the trade-off between repeating frames and a longer, more time-consuming, data stream is advantageous.

It should be readily apparent, that if the capsule is moving too slowly, an inordinate number of frames may be identical. If that is the case, the frame rate controller, based on the pixel comparisons of the image processor, can speed up the display rate by eliminating one or more identical frames.

It should also be readily apparent that the above-described methods for varying frame capture and display rates can be applied to video endoscopes with little or no modification.

It will be appreciated by persons skilled in the art that the present invention is not limited by what has been particularly shown and described herein above. Rather the scope of the invention is defined by the claims that follow:

The invention claimed is:

1. An in vivo camera system comprising:
  a swallowable capsule for obtaining images from within a patient's gastrointestinal tract, the capsule comprising an imager adapted to have its frame capture rate varied;
  a processor to measure the movement of the capsule by comparing at least two images obtained thereby; and
  a transmitter external to the patient, the transmitter to transmit to the capsule a frame capture rate, the imager to capture frames at the frame capture rate, which is lower when the capsule movement is relatively slow and faster when the capsule movement is relatively fast.

2. The system according to claim 1, wherein the processor is to provide the capture rate to said transmitter.

3. An in vivo camera system comprising:
  a swallowable capsule for obtaining images from within a patient's gastrointestinal tract, the capsule comprising an imager adapted to have its frame capture rate varied;
  a processor to determine a frame capture rate for the capsule by comparing at least two images obtained thereby; and
  a transmitter in communication with said processor, the transmitter external to the patient, the transmitter to transmit to the capsule the frame capture rate, the imager to capture frames at the frame capture rate, wherein the frame capture rate is lower when the capsule movement is relatively slow and faster when the capsule movement is relatively fast.

4. The system according to claim 3 wherein the processor is to provide the capture rate to said transmitter.

\* \* \* \* \*